United States Patent [19]

Schulz et al.

[11] Patent Number: 4,678,504

[45] Date of Patent: Jul. 7, 1987

[54] O-SUBSTITUTED 3-OXYPRIDINIUM SALTS, THEIR PREPARATION AND THEIR USE AS FUNGICIDES FOR CROP PROTECTION

[75] Inventors: Guenter Schulz; Eberhard Ammermann, both of Ludwigshafen; Ernst-Heinrich Pommer, Limburgerhof, all of Fed. Rep. of Germany

[73] Assignee: BASF Aktiengesellschaft, Ludwigshafen, Fed. Rep. of Germany

[21] Appl. No.: 878,218

[22] Filed: Jun. 25, 1986

[30] Foreign Application Priority Data

Jun. 27, 1985 [DE] Fed. Rep. of Germany ....... 3522905

[51] Int. Cl.$^4$ ................. A01N 43/40; C07D 213/02
[52] U.S. Cl. ........................................ 71/94; 546/290; 546/300; 546/301; 546/302; 546/303
[58] Field of Search ............... 546/290, 300, 301, 302, 546/303; 71/94

[56] References Cited

PUBLICATIONS

Chem. Abstracts 105(7):60578r.

Primary Examiner—John M. Ford
Assistant Examiner—J. Richter
Attorney, Agent, or Firm—Keil & Weinkauf

[57] ABSTRACT

O-substituted 3-oxypyridinium salts of the formula

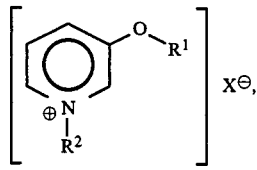

where $R^1$ is unsubstituted alkyl, alkenyl or alkynyl, or is aralkyl, $R^3$ is hydrogen, alkyl, alkenyl or alkoxy, $R^2$ is substituted or unsubstituted alkyl, alkenyl or alkynyl, or is aralkyl, and $X^\ominus$ is an anion, and fungicides for crop protection containing these compounds.

4 Claims, No Drawings

O-SUBSTITUTED 3-OXYPRIDINIUM SALTS, THEIR PREPARATION AND THEIR USE AS FUNGICIDES FOR CROP PROTECTION

The present invention relates to novel O-substituted 3-oxypyridinium salts, a process for their preparation and fungicides for crop protection which contain these compounds.

It is known that N-trichloromethylthio-tetrahydrophthalimide can be used as a fungicide (Chemical Week, June 21, 1972, page 46), but its action is poor.

We have found that O-substituted 3-oxypyridinium salts of the formula

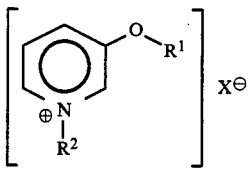

where $R^1$ is an alkyl, alkenyl or alkynyl radical which contains a total of 8 to 20 carbon atoms and is unsubstituted or substituted by alkoxy or halogen, or $R^1$ is

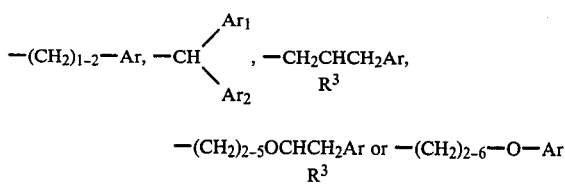

$$-(CH_2)_{2-5}OCHCH_2Ar \text{ or } -(CH_2)_{2-6}-O-Ar$$
$$\phantom{-(CH_2)_{2-5}O}R^3$$

where Ar, $Ar_1$ and $Ar_2$ are each 1- or 2-naphthyl, biphenyl or phenyl, and the phenyl radical may be substituted by F, Cl, Br, $NO_2$, $CF_3$, CN, $C_1$-$C_{13}$—alkyl, $C_2$-$C_4$-alkenyl or $C_1$— or $C_2$—alkoxy and $R^3$ is H, $C_1$—or $C_2$—alkyl, $C_3$-$C_5$—alkenyl or $C_1$-$C_5$—alkoxy, $R^2$ is an alkyl, alkenyl or alkynyl radical of 1 or 2 or 3 to 8 carbon atoms which is unsubstituted or substituted by $C_1$-$C_4$—alkoxy or halogen, or $R^2$ is

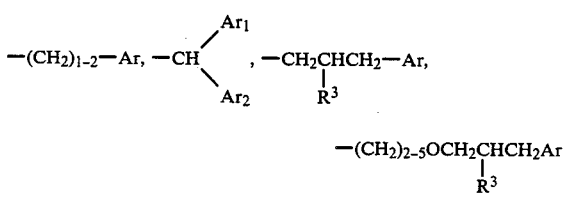

$$-(CH_2)_{2-5}OCH_2CHCH_2Ar$$
$$\phantom{-(CH_2)_{2-5}OCH_2}R^3$$

or $-(CH_2)_{2-6}-O-Ar$, where Ar, $Ar_1$ and $Ar_2$ are each 1- or 2-naphthyl, biphenyl or phenyl, and the phenyl radical may be substituted by F, Cl, Br, $NO_2$, $CF_3$, CN, $C_1$-$C_{13}$—alkyl $C_2$-$C_4$-alkenyl or $C_1$— or $C_2$—alkoxy, and $X^-$ is $F^-$, $Cl^-$, $Br^-$ or $I^-$ or one equivalent of an anion of a nonphytotoxic acid, have a good fungicidal activity against phytophathogenic fungi.

$R^1$ is, for example, straight-chain or branched $C_8$-$C_{18}$—alkyl, in particular $C_{10}$-$C_{18}$—alkyl, eg. octyl, nonyl decyl, undecyl, dodecyl, tridecyl, tetradecyl, pentadecyl, hexadecyl, heptadecyl or octadecyl, which is unsubstituted or substituted by 2–5 Cl or F atoms, or is $-C_2$-$C_{10}$—alkyl—O—$C_5$-$C_{18}$—alkyl which contains a total of 10 to 20 carbon atoms and may contain 1 or 2 double bonds or one triple bond which are or is separated from 0 by one or more $CH_2$ groups, eg. 5-decenyl, 8-octadecenyl or 5-dodecynyl, or a radical

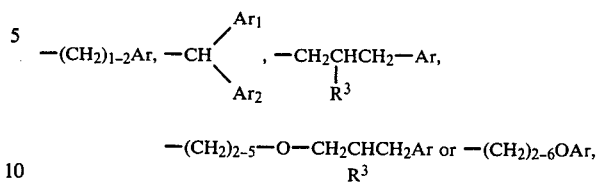

$$-(CH_2)_{2-5}-O-CH_2CHCH_2Ar \text{ or } -(CH_2)_{2-6}OAr,$$
$$\phantom{-(CH_2)_{2-5}-O-CH_2}R^3$$

where Ar, $Ar_1$ and $Ar_2$ are each 1- or 2-naphthyl, biphenyl, phenyl, monosubstituted, disubstituted or trisubstituted phenyl, eg. 4-fluorophenyl, 3- or 4-chlorophenyl, 4-bromochlorophenyl, 3,4-dichlorphenyl, 2,4-dichlorphenyl, 2,6-dichlorophenyl, 2,4,6-trichlorophenyl, 2-methyl-4-chlorophenyl, 4-methoxyphenyl, 4-ethoxyphenyl, 4-methylphenyl, 4-nitrophenyl, 4-tert.-butylphenyl, 4-dodecylphenyl, 4-trifluoromethylphenyl, 2-trifluoromethyl-4-chlorophenyl, 2,4-dimethylphenyl, 2,4,6-trimethylphenyl or 4-cyanophenyl, $R^3$ is, for example, hydrogen, methyl or ethyl, $R^2$ is, for example, methyl, ethyl, propyl, isopropyl, n-butyl, isobutyl, n-pentyl, isopentyl, n-hexyl, allyl, 2-chloropropenyl, 2-bromophenyl, 3-chloropropenyl, but-2-en-1-yl, 3-methylbut-2-en-1-yl, 2-methylpropenyl, 3-chlorobut-2-en-1-yl, propargyl or a radical

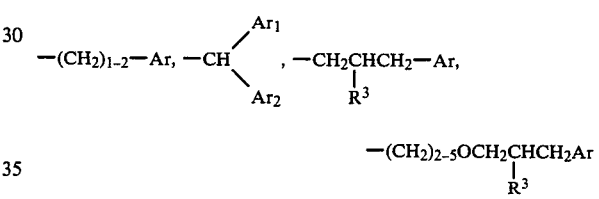

$$-(CH_2)_{2-5}OCH_2CHCH_2Ar$$
$$\phantom{-(CH_2)_{2-5}OCH_2}R^3$$

or $-(CH_2)_{2-6}OAr$, where Ar, $Ar_1$ and $Ar_2$ are each 1- or 2-naphthyl, biphenyl, phenyl, monosubstituted, disubstituted or trisubstituted phenyl, eg. 4-fluorophenyl, 3- or 4-chlorophenyl, 4-bromophenyl, 3,4-dichlorophenyl, 2,4-dichlorophenyl, 2,6-dichlorophenyl, 2,4,6-trichlorophenyl, 2-methyl-4-chlorophenyl, 4-methoxyphenyl, 4-ethoxyphenyl, 4-methylphenyl, 4-nitrophenyl, 4-tert.-butylphenyl, 4-dodecylphenyl, 4-trifluoromethylphenyl, 2-trifluoromethyl-4-chlorophenyl, 2,4-dimethylphenyl, 2,4,6-trimethylphenyl or 4-cyanophenyl, and $X^\ominus$ is $Cl^\ominus$, $Br^\ominus$, $I^\ominus$ or one equivalent of an anion of a nonphytotoxic acid, such as phenylsulfonic acid, p-methylphenylsulfonic acid or one equivalent of the anion of sulfuric acid.

The O-substituted 3-oxypyridinium salts of the formula I are obtained by reacting a compound of the formula

$$R^2X \qquad\qquad II$$

where $R^2$ and X have the above meanings, with an O-substituted 3-oxypyridine derivative of the formula

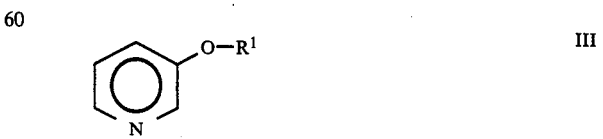

where $R^1$ has the above meanings.

The reaction is carried out in the absence of a diluent or in the presence of an inert solvent or diluent at from 20° to 150° C. or preferably from 50° to 150° C. The starting material of formula III is advantageously reacted with up to 10 times the (molar) amount, based on the starting material III, of the alkylating agent of the formula II.

Preferably used solvents or diluents which are inert to the reactants are, for example, aliphatic or aromatic hydrocarbons and halohydrocarbons, such as pentane, cyclohexane, heptane, benzene, toluene, xylene, chlorobenzene or dichlorobenzenes, aliphatic ketones, such as acetone, methyl ethyl ketone, diethyl ketone or cyclopentanone, ethers, such as diethyl ether, methyl tert-butyl ether, dimethoxyethane, tetrahydrofuran or dioxane, esters, such as ethyl acetate, nitriles, such as acetonitrile, amides, such as dimethylformamide, dimethylacetamide and N-methylpyrrolidone, and mixtures of these solvents.

The starting materials of the formulae II and III are substantially known and some of them are available commercially; those which are unknown can be prepared by methods similar to examples described in the literature (in the case of III, for example, according to Chem. Ber. 116, (1983), 2394).

The novel O-substituted 3-oxypyridinium salts may possess a chiral carbon atom in $R^1$ and/or $R^2$ when $R^3$ is not hydrogen. The optically pure enantiomers or the diastereomers can be obtained by the conventional methods. The present invention embraces these compounds in pure form as well as mixtures of them. Both the pure enantiomers or the pure diastereomers and the mixtures usually obtained in the synthesis are effective.

The Examples which follow illustrate the preparation of the novel compounds.

PREPARATION EXAMPLE 1

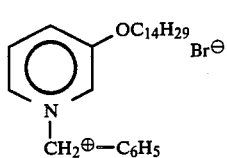

(a)

Starting material

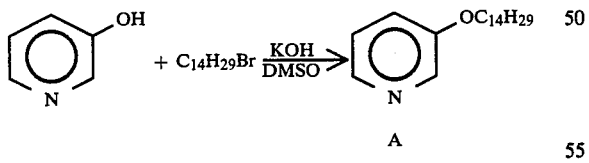

100 g (1.04 moles) of 3-hydroxypyridine in 500 ml of dimethyl sulfoxide (DMSO) are stirred with 87.4 g (1.56 moles) of KOH powder under nitrogen at room temperature (20° C.). After about 30 minutes, 360 g (1.3 moles) of tetradecyl bromide are added dropwise, and the mixture is stirred for 4 hours at room temperature. The reaction mixture is poured into 1 l of water and extracted with three times 500 ml of methylene chloride. The combined extracts are washed twice with 1 l of water, dried with $Na_2SO_4$ and evaporated down. Filtration over silica gel with n-pentane and methyl chloride gives 144 g of product A of melting point 36° C.

(b)

Pyridinium salt formation

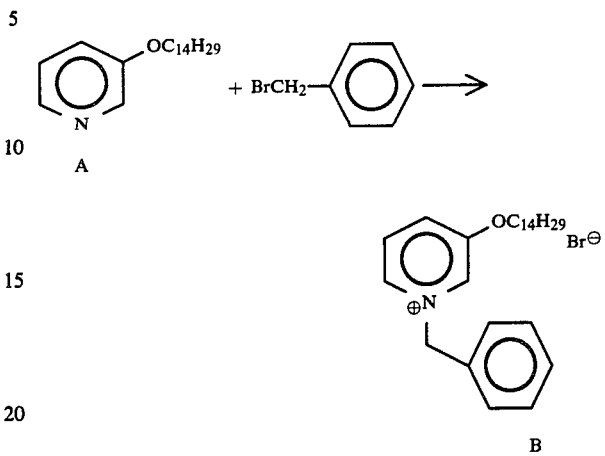

11.5 g (0.04 mole) of 3-tetradecyloxypyridine (A) are stirred with 5 ml (0.04 mole) of benzyl bromide for 20 minutes at 100°–120° C. The mixture is cooled to room temperature and then suspended in pentane, and the product is filtered off under suction, washed with pentane and dried, 16.8 g of pyridinium salt B of melting point 129° C. being obtained (compound No. 23).

PREPARATION EXAMPLE 2

(a)

Starting material

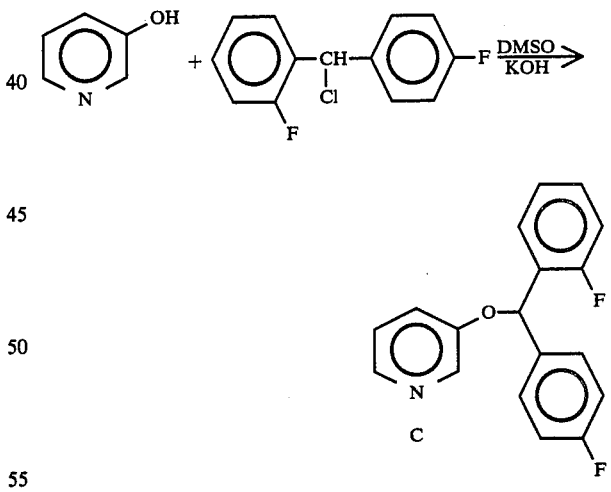

19 g of 3-hydroxypyridine in 200 ml of DMSO are stirred with 33.6 g of KOH powder. After 30 minutes, 59.6 g of 2,4'-difluorobenzhydryl chloride are added dropwise at room temperature. After 40 minutes, the reaction mixture is poured into ice water and extracted with three times 300 ml of ether. The product is precipitated as the bisulfate by carefully adding concentrated $H_2SO_4$. Ether is decanted, and the product is liberated with bicarbonate and taken up in methylene chloride, and the solution is dried with $Na_2SO_4$ and evaporated down to give 38.5 g of C in the form of an oil.

(b) Cl Formation of the pyridinium salt

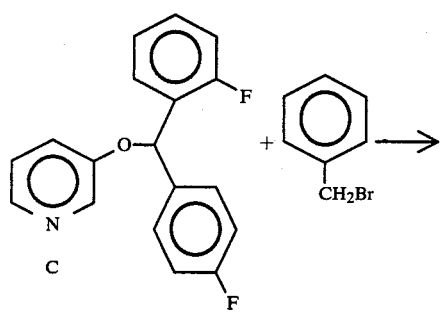

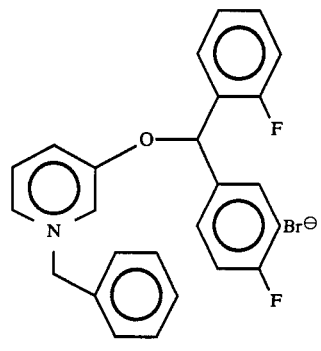

10 g of C in 100 ml of dimethylformamide (DMF) are stirred with 5.8 g of benzyl bromide. After about 1 hour, the DMF is distilled off under reduced pressure, the residue is suspended in pentane and the suspension is filtered under suction to give 14.4 g of compound D of melting point 173° C. (compound No. 165).

The compounds listed in the Table below can be prepared in a similar manner:

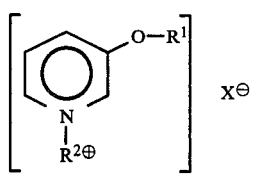

| No. | R¹ | R² | X | m.p. [°C.] |
|---|---|---|---|---|
| 1 | n-$C_{10}H_{21}$ | $CH_3$ | Cl | |
| 2 | n-$C_{10}H_{21}$ | $CH_3$ | Br | |
| 3 | n-$C_{10}H_{21}$ | $CH_3$ | I | |
| 4 | n-$C_{12}H_{25}$ | $CH_3$ | Br | |
| 5 | n-$C_{12}H_{25}$ | $CH_3$ | I | 64–71 |
| 6 | n-$C_{12}H_{25}$ | $-CH_2-CH=CH_2$ | Br | 69 |
| 7 | n-$C_{12}H_{25}$ | $-CH_2-C_6H_5$ | Br | 61–65 |
| 8 | n-$C_{12}H_{25}$ | $-CH_2-C_6H_5$ | Cl | |
| 9 | n-$C_{12}H_{25}$ | $-CH_2-(2-Cl-C_6H_4)$ | Cl | 89 |
| 10 | n-$C_{12}H_{25}$ | $-CH_2-(3-Cl-C_6H_4)$ | Cl | |
| 11 | n-$C_{12}H_{25}$ | $-CH_2-(4-Cl-C_6H_4)$ | Cl | 93 |
| 12 | n-$C_{12}H_{25}$ | $-CH_2CH_2O-(2-Cl-C_6H_4)$ | Br | 94 |
| 13 | n-$C_{12}H_{25}$ | $-CH_2CH_2O-(3-Cl-C_6H_4)$ | Br | 146 |
| 14 | n-$C_{12}H_{25}$ | $-CH_2CH_2O-(4-Cl-C_6H_4)$ | Br | 135 |
| 15 | n-$C_{12}H_{25}$ | $-CH_2-CH=CHCl$ | Cl | |
| 16 | n-$C_{12}H_{25}$ | $-CH_2-C\equiv CH$ | Br | |
| 17 | n-$C_{12}H_{25}$ | $-CH_2CH=CH-CH_3$ | Cl | |
| 18 | n-$C_{12}H_{25}$ | $-CH_2CCl=CH_2$ | Br | |
| 19 | n-$C_{12}H_{25}$ | $-CH_2CCl=CCl_2$ | Br | |
| 20 | n-$C_{14}H_{29}$ | $CH_3$ | Br | |
| 21 | n-$C_{14}H_{29}$ | $CH_3$ | Cl | |
| 22 | n-$C_{14}H_{29}$ | $CH_3$ | I | 91–95 |
| 23 | n-$C_{14}H_{29}$ | $-CH_2C_6H_5$ | Br | 129 |
| 24 | n-$C_{14}H_{29}$ | $-CH_2C_6H_5$ | Cl | |
| 25 | n-$C_{14}H_{29}$ | $-CH_2-(2-Cl-C_6H_4)$ | Cl | 92 |
| 26 | n-$C_{14}H_{29}$ | $-CH_2-(3-Cl-C_6H_4)$ | Cl | |
| 27 | n-$C_{14}H_{29}$ | $-CH_2-(4-Cl-C_6H_4)$ | Cl | 115 |
| 28 | n-$C_{14}H_{29}$ | $-CH_2CH_2O-(2-Cl-C_6H_4)$ | Br | 97 |
| 29 | n-$C_{14}H_{29}$ | $-CH_2CH_2O-(3-Cl-C_6H_4)$ | Br | 144 |
| 30 | n-$C_{14}H_{29}$ | $-CH_2CH_2O-(4-Cl-C_6H_4)$ | Br | 133 |
| 31 | n-$C_{14}H_{29}$ | $-CH_2-CH=CH_2$ | Cl | |
| 32 | n-$C_{14}H_{29}$ | $-CH_2-CH=CH_2$ | Br | 83 |
| 33 | n-$C_{14}H_{29}$ | $-CH_2-CH=CHCl$ | Cl | |
| 34 | n-$C_{14}H_{29}$ | $-CH_2-CH=CH-CH_3$ | Cl | |
| 35 | n-$C_{14}H_{29}$ | $-CH_2-CCl=CCl_2$ | Cl | |
| 36 | n-$C_{14}H_{29}$ | propargyl | Br | |
| 37 | n-$C_{14}H_{29}$ | propargyl | Cl | |
| 38 | n-$C_{16}H_{33}$ | $CH_3$ | Br | |
| 39 | n-$C_{16}H_{33}$ | $CH_3$ | Cl | |
| 40 | n-$C_{16}H_{33}$ | $CH_3$ | I | 96–101 |

-continued

| | | | | |
|---|---|---|---|---|
| 41 | n-C$_{16}$H$_{33}$ | —CH$_2$C$_6$H$_5$ | Br | 57–60 |
| 42 | n-C$_{16}$H$_{33}$ | —CH$_2$C$_6$H$_5$ | Cl | |
| 43 | n-C$_{16}$H$_{33}$ | —CH$_2$—(2-Cl—C$_6$H$_4$) | Cl | |
| 44 | n-C$_{16}$H$_{33}$ | —CH$_2$—(3-Cl—C$_6$H$_4$) | Cl | |
| 45 | n-C$_{16}$H$_{33}$ | —CH$_2$—(4-Cl—C$_6$H$_4$) | Cl | |
| 46 | n-C$_{16}$H$_{33}$ | —CH$_2$CH$_2$O—(2-Cl—C$_6$H$_4$) | Br | |
| 47 | n-C$_{16}$H$_{33}$ | —CH$_2$CH$_2$O—(3-Cl—C$_6$H$_4$) | Br | |
| 48 | n-C$_{16}$H$_{33}$ | —CH$_2$CH$_2$O—(4-Cl—C$_6$H$_4$) | Br | |
| 49 | n-C$_{16}$H$_{33}$ | —CH$_2$CH$_2$O—C$_6$H$_5$ | Br | |
| 50 | n-C$_{14}$H$_{29}$ | —CH$_2$CH$_2$O—C$_6$H$_5$ | Br | |
| 51 | n-C$_{12}$H$_{25}$ | —CH$_2$CH$_2$O—C$_6$H$_5$ | Br | |
| 52 | n-C$_{10}$H$_{21}$ | —CH$_2$CH$_2$O—C$_6$H$_5$ | Br | |
| 53 | n-C$_{16}$H$_{33}$ | —CH$_2$CH=CH$_2$ | Cl | |
| 54 | n-C$_{16}$H$_{33}$ | —CH$_2$CH=CHCl | Cl | |
| 55 | n-C$_{16}$H$_{33}$ | —CH$_2$CH=CH—CH$_3$ | Cl | |
| 56 | n-C$_{16}$H$_{33}$ | —CH$_2$—CCl=CCl$_2$ | Cl | |
| 57 | n-C$_{16}$H$_{33}$ | propargyl | Br | |
| 58 | n-C$_{18}$H$_{37}$ | CH$_3$ | Br | |
| 59 | n-C$_{18}$H$_{37}$ | CH$_3$ | Cl | |
| 60 | n-C$_{18}$H$_{37}$ | CH$_3$ | I | 89 |
| 61 | n-C$_{18}$H$_{37}$ | —CH$_2$—C$_6$H$_5$ | Br | 71–74 |
| 62 | n-C$_{18}$H$_{37}$ | —CH$_2$—C$_6$H$_5$ | Cl | |
| 63 | n-C$_{18}$H$_{37}$ | —CH$_2$—(2-Cl—C$_6$H$_4$) | Cl | |
| 64 | n-C$_{18}$H$_{37}$ | —CH$_2$—(3-Cl—C$_6$H$_4$) | Cl | |
| 65 | n-C$_{18}$H$_{37}$ | —CH$_2$—(4-Cl—C$_6$H$_4$) | Cl | |
| 66 | n-C$_{18}$H$_{37}$ | —CH$_2$CH$_2$O—C$_6$H$_5$ | Br | |
| 67 | n-C$_{18}$H$_{37}$ | —CH$_2$CH$_2$O—(2-Cl—C$_6$H$_4$) | Br | |
| 68 | n-C$_{18}$H$_{37}$ | —CH$_2$CH$_2$O—(3-Cl—C$_6$H$_4$) | Br | |
| 69 | n-C$_{18}$H$_{37}$ | —CH$_2$CH$_2$O—(4-Cl—C$_6$H$_4$) | Br | |
| 70 | n-C$_{18}$H$_{37}$ | —CH$_2$—CH=CH$_2$ | Br | |
| 71 | n-C$_{18}$H$_{37}$ | —CH$_2$—CH=CH—Cl | Cl | |
| 72 | n-C$_{18}$H$_{37}$ | —CH$_2$—CH=CH—CH$_3$ | Cl | |
| 73 | n-C$_{18}$H$_{37}$ | —CH$_2$—CCl=CCl$_2$ | Cl | |
| 74 | n-C$_{18}$H$_{37}$ | propargyl | Br | |
| 75 | n-C$_{20}$H$_{41}$ | CH$_3$ | Br | |
| 76 | n-C$_{20}$H$_{41}$ | CH$_3$ | I | |
| 77 | n-C$_{20}$H$_{41}$ | CH$_3$ | Cl | |
| 78 | n-C$_{20}$H$_{41}$ | —CH$_2$C$_6$H$_5$ | Cl | |
| 79 | n-C$_{20}$H$_{41}$ | —CH$_2$C$_6$H$_5$ | Br | |
| 80 | —C$_{20}$H$_{41}$ | —CH$_2$CH$_2$—O—C$_6$H$_5$ | Br | |
| 81 | —(CH$_2$)$_4$—O—(CH$_2$)$_7$—CH$_3$ | —CH$_3$ | Br | |
| 82 | —(CH$_2$)$_4$—O—(CH$_2$)$_7$—CH$_3$ | —CH$_3$ | I | |
| 83 | —(CH$_2$)$_4$—O—(CH$_2$)$_7$—CH$_3$ | —CH$_2$—C$_6$H$_5$ | Cl | |
| 84 | —(CH$_2$)$_4$—O—(CH$_2$)$_7$—CH$_3$ | —CH$_2$—C$_6$H$_5$ | Br | 79 |
| 85 | —(CH$_2$)$_4$—O—(CH$_2$)$_7$—CH$_3$ | —CH$_2$CH$_2$O—C$_6$H$_5$ | Br | |
| 86 | —(CH$_2$)$_4$—O—(CH$_2$)$_7$—CH$_3$ | —CH$_2$—CH=CH$_2$ | Br | |
| 87 | —(CH$_2$)$_4$—O(CH$_2$)$_{10}$CH$_3$ | —CH$_3$ | Br | |
| 88 | —(CH$_2$)$_4$—O(CH$_2$)$_{10}$CH$_3$ | —CH$_3$ | I | 105 |
| 89 | —(CH$_2$)$_4$—O(CH$_2$)$_{10}$CH$_3$ | —CH$_2$—C$_6$H$_5$ | Cl | |
| 90 | —(CH$_2$)$_4$—O(CH$_2$)$_{10}$CH$_3$ | —CH$_2$—C$_6$H$_5$ | Br | |
| 91 | —(CH$_2$)$_4$—O(CH$_2$)$_{10}$CH$_3$ | —CH$_2$CH$_2$O—C$_6$H$_5$ | Br | |
| 92 | —(CH$_2$)$_4$—O(CH$_2$)$_{10}$CH$_3$ | —CH$_2$—CH=CH$_2$ | Cl | |
| 93 | —(CH$_2$)$_5$—O—CH$_2$CH(C$_2$H$_5$)CH$_2$CH(CH$_3$)$_2$ | CH$_3$ | Br | |
| 94 | —(CH$_2$)$_5$—O—CH$_2$CH(C$_2$H$_5$)CH$_2$CH(CH$_3$)$_2$ | CH$_3$ | I | |
| 95 | —(CH$_2$)$_5$—O—CH$_2$CH(C$_2$H$_5$)CH$_2$CH(CH$_3$)$_2$ | —CH$_2$CH=CH$_2$ | Br | |
| 96 | —(CH$_2$)$_5$—O—CH$_2$CH(C$_2$H$_5$)CH$_2$CH(CH$_3$)$_2$ | —CH$_2$C$_6$H$_5$ | Br | oil |
| 97 | —(CH$_2$)$_5$—O—CH$_2$CH(C$_2$H$_5$)CH$_2$CH(CH$_3$)$_2$ | —CH$_2$CH$_2$O—C$_6$H$_5$ | Br | |
| 98 | —(CH$_2$)$_6$—O—CH$_2$CH(CH$_3$)CH$_2$CH(CH$_3$)$_2$ | CH$_3$ | I | |
| 99 | —(CH$_2$)$_6$—O—CH$_2$CH(CH$_3$)CH$_2$CH(CH$_3$)$_2$ | CH$_3$ | Br | |
| 100 | —(CH$_2$)$_6$—O—CH$_2$CH(CH$_3$)CH$_2$CH(CH$_3$)$_2$ | —CH$_2$—C$_6$H$_5$ | Br | |
| 101 | —(CH$_2$)$_6$—O—CH$_2$CH(CH$_3$)CH$_2$CH(CH$_3$)$_2$ | —CH$_2$—C$_6$H$_5$ | Cl | |
| 102 | —(CH$_2$)$_6$—O—CH$_2$CH(CH$_3$)CH$_2$CH(CH$_3$)$_2$ | —CH$_2$CH$_2$O—C$_6$H$_5$ | Br | |
| 103 | —(CH$_2$)$_6$—O—CH$_2$CH(CH$_3$)CH$_2$CH(CH$_3$)$_2$ | —CH$_2$CH=CH$_2$ | Br | |
| 104 | —(CH$_2$)$_6$—O—CH(CH$_3$)CH$_2$CH$_2$CH(C$_2$H$_5$)$_2$ | —CH$_3$ | Br | |
| 105 | —(CH$_2$)$_6$—O—CH(CH$_3$)CH$_2$CH$_2$CH(C$_2$H$_5$)$_2$ | —CH$_3$ | I | |
| 106 | —(CH$_2$)$_6$—O—CH(CH$_3$)CH$_2$CH$_2$CH(C$_2$H$_5$)$_2$ | —CH$_2$C$_6$H$_5$ | Br | |
| 107 | —(CH$_2$)$_6$—O—CH(CH$_3$)CH$_2$CH$_2$CH(C$_2$H$_5$)$_2$ | —CH$_2$C$_6$H$_5$ | Cl | |
| 108 | —(CH$_2$)$_6$—O—CH(CH$_3$)CH$_2$CH$_2$CH(C$_2$H$_5$)$_2$ | —CH$_2$CH$_2$OC$_6$H$_5$ | Br | |
| 109 | —(CH$_2$)$_6$—O—CH(CH$_3$)CH$_2$CH$_2$CH(C$_2$H$_5$)$_2$ | —CH$_2$CH=CH$_2$ | Br | |
| 110 | —(CH$_2$)$_5$—O—CH$_2$CH$_2$CH(C$_2$H$_5$)(CH$_2$)$_3$CH$_3$ | —CH$_3$ | I | |
| 111 | —(CH$_2$)$_5$—O—CH$_2$CH$_2$CH(C$_2$H$_5$)(CH$_2$)$_3$CH$_3$ | —CH$_3$ | Br | |
| 112 | —(CH$_2$)$_5$—O—CH$_2$CH$_2$CH(C$_2$H$_5$)(CH$_2$)$_3$CH$_3$ | —CH$_2$C$_6$H$_5$ | Cl | |
| 113 | —(CH$_2$)$_5$—O—CH$_2$CH$_2$CH(C$_2$H$_5$)(CH$_2$)$_3$CH$_3$ | —CH$_2$C$_6$H$_5$ | Br | |
| 114 | —(CH$_2$)$_5$—O—CH$_2$CH$_2$CH(C$_2$H$_5$)(CH$_2$)$_3$CH$_3$ | —CH$_2$CH=CH$_2$ | Br | |
| 115 | —(CH$_2$)$_5$—O—CH$_2$CH$_2$CH(C$_2$H$_5$)(CH$_2$)$_3$CH$_3$ | —CH$_2$CH$_2$O—C$_6$H$_5$ | Br | |
| 116 | —(CH$_2$)$_6$—O—(CH$_2$)$_2$CH(CH$_3$)(CH$_2$)$_3$CH(CH$_3$)$_2$ | CH$_3$ | Br | |
| 117 | —(CH$_2$)$_6$—O—(CH$_2$)$_2$CH(CH$_3$)(CH$_2$)$_3$CH(CH$_3$)$_2$ | CH$_3$ | I | |
| 118 | —(CH$_2$)$_6$—O—(CH$_2$)$_2$CH(CH$_3$)(CH$_2$)$_3$CH(CH$_3$)$_2$ | —CH$_2$C$_6$H$_5$ | Cl | |
| 119 | —(CH$_2$)$_6$—O—(CH$_2$)$_2$CH(CH$_3$)(CH$_2$)$_3$CH(CH$_3$)$_2$ | —CH$_2$C$_6$H$_5$ | Br | oil |

-continued

| No. | | | | |
|---|---|---|---|---|
| 120 | $-(CH_2)_6-O-(CH_2)_2CH(CH_3)(CH_2)_3CH(CH_3)_2$ | $-CH_2CH=CH_2$ | Br | |
| 121 | $-(CH_2)_6-O-(CH_2)_2CH(CH_3)(CH_2)_3CH(CH_3)_2$ | $-CH_2CH_2O-C_6H_5$ | Br | |
| 122 | $-(CH_2)_4-O-(CH_2)_2CH(CH_3)(CH_2)_3CH(CH_3)(CH_2)_3CH(CH_3)_2$ | $CH_3$ | Br | |
| 123 | $-(CH_2)_4-O-(CH_2)_2CH(CH_3)(CH_2)_3CH(CH_3)(CH_2)_3CH(CH_3)_2$ | $CH_3$ | I | |
| 124 | $-(CH_2)_4-O-(CH_2)_2CH(CH_3)(CH_2)_3CH(CH_3)(CH_2)_3CH(CH_3)_2$ | $-CH_2C_6H_5$ | Br | |
| 125 | $-(CH_2)_4-O-(CH_2)_2CH(CH_3)(CH_2)_3CH(CH_3)(CH_2)_3CH(CH_3)_2$ | $-CH_2C_6H_5$ | Cl | |
| 126 | $-(CH_2)_4-O-(CH_2)_2CH(CH_3)(CH_2)_3CH(CH_3)(CH_2)_3CH(CH_3)_2$ | $-CH_2CH=CH_2$ | Br | |
| 127 | $-(CH_2)_4-O-(CH_2)_2CH(CH_3)(CH_2)_3CH(CH_3)(CH_2)_3CH(CH_3)_2$ | $-CH_2CH_2O-C_6H_5$ | Br | |
| 128 | $-(CH_2)_4O-(2-CH(CH_3)_2-5-CH_3-cycl.C_6H_9)$ | $CH_2C_6H_5$ | Br | 135 |
| 129 | $-(CH_2)_4O-(2-CH(CH_3)_2-5-CH_3-cycl.C_6H_9)$ | $CH_3$ | Br | |
| 130 | $-(CH_2)_4O-(2-CH(CH_3)_2-5-CH_3-cycl.C_6H_9)$ | $CH_3$ | I | |
| 131 | $-(CH_2)_4O-(2-CH(CH_3)_2-5-CH_3-cycl.C_6H_9)$ | $-CH_2-CH=CH_2$ | Br | |
| 132 | $-(CH_2)_6-O-(4\text{-tert.}-C_4H_9-cycl.C_6H_{10})$ | $-CH_3$ | Br | |
| 133 | $-(CH_2)_6-O-(4\text{-tert.}C_4H_9-cycl.C_6H_{10})$ | $-CH_3$ | I | 96 |
| 134 | $-(CH_2)_6-O-(4\text{-tert.}C_4H_9-cycl.C_6H_{10})$ | $-CH_2C_6H_5$ | Br | 116 |
| 135 | $-(CH_2)_6-O-(4\text{-tert.}C_4H_9-cycl.C_6H_{10})$ | $-CH_2C_6H_5$ | Cl | |
| 136 | $-(CH_2)_6-O-(4\text{-tert.}C_4H_9-cycl.C_6H_{10})$ | $-CH_2CH=CH_2$ | Br | |
| 137 | $-(CH_2)_4-O-CH_2CH(CH_3)CH_2-C_6H_5$ | $-CH_3$ | I | oil |
| 138 | $-(CH_2)_4-O-CH_2CH(CH_3)CH_2-C_6H_5$ | $-CH_3$ | Br | |
| 139 | $-(CH_2)_4-O-CH_2CH(CH_3)CH_2-C_6H_5$ | $-CH_2C_6H_5$ | Br | 110 |
| 140 | $-(CH_2)_4-O-CH_2CH(CH_3)CH_2-C_6H_5$ | $-CH_2C_6H_5$ | Cl | |
| 141 | $-(CH_2)_4-O-CH_2CH(CH_3)CH_2-C_6H_5$ | $-CH_2CH=CH_2$ | Br | |

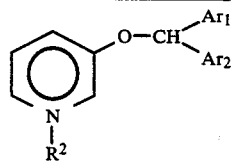

| No. | Ar$^1$ | Ar$^2$ | R$^2$ | X | m.p. [°C.] |
|---|---|---|---|---|---|
| 142 | $-C_6H_5$ | $-C_6H_5$ | $CH_3$ | I | |
| 143 | $-C_6H_5$ | $-C_6H_5$ | $CH_3$ | Br | |
| 144 | $-C_6H_5$ | $-C_6H_5$ | $-CH_2CH=CH_2$ | Br | |
| 145 | $-C_6H_5$ | $-C_6H_5$ | $-CH_2C_6H_5$ | Br | |
| 146 | $-C_6H_5$ | $-(4\text{-Cl})C_6H_4$ | $CH_3$ | I | 110–111 |
| 147 | $-C_6H_5$ | $-(4\text{-Cl})C_6H_4$ | $CH_3$ | Br | |
| 148 | $-C_6H_5$ | $-(4\text{-Cl})C_6H_4$ | $-CH_2CH=CH_2$ | Br | |
| 149 | $-C_6H_5$ | $-(4\text{-Cl})C_6H_4$ | $-CH_2-C_6H_5$ | Br | oil |
| 150 | $-(4\text{-Cl})C_6H_4$ | $-(4\text{-Cl})C_6H_4$ | $CH_3$ | Br | |
| 151 | $-(4\text{-Cl})C_6H_4$ | $-(4\text{-Cl})C_6H_4$ | $CH_3$ | I | 190 |
| 152 | $-(4\text{-Cl})C_6H_4$ | $-(4\text{-Cl})C_6H_4$ | $-CH_2-CH=CH_2$ | Br | |
| 153 | $-(4\text{-Cl})C_6H_4$ | $-(4\text{-Cl})C_6H_4$ | $-CH_2-C_6H_5$ | Br | 71 |
| 154 | $-C_6H_5$ | $-(3\text{-CF}_3)C_6H_4$ | $CH_3$ | Br | |
| 155 | $-C_6H_5$ | $-(3\text{-CF}_3)C_6H_4$ | $CH_3$ | I | 161 |
| 156 | $-C_6H_5$ | $-(3\text{-CF}_3)C_6H_4$ | $-CH_2CH=CH_2$ | Br | |
| 157 | $-C_6H_5$ | $-(3\text{-CF}_3)C_6H_4$ | $-CH_2-C_6H_5$ | Br | oil |
| 158 | $-(4\text{-F})C_6H_4$ | $-(2,4\text{-Cl}_2)C_6H_3$ | $CH_3$ | Br | |
| 159 | $-(4\text{-F})C_6H_4$ | $-(2,4\text{-Cl}_2)C_6H_3$ | $CH_3$ | I | 65–66 |
| 160 | $-(4\text{-F})C_6H_4$ | $-(2,4\text{-Cl}_2)C_6H_3$ | $-CH_2-CH=CH_2$ | Br | |
| 161 | $-(4\text{-F})C_6H_4$ | $-(2,4\text{-Cl}_2)C_6H_3$ | $-CH_2C_6H_5$ | Br | 90 |
| 162 | $-(2\text{-F})C_6H_4$ | $-(4\text{-F})C_6H_4$ | $CH_3$ | Br | |
| 163 | $-(2\text{-F})C_6H_4$ | $-(4\text{-F})C_6H_4$ | $CH_3$ | I | 143 |
| 164 | $-(2\text{-F})C_6H_4$ | $-(4\text{-F})C_6H_4$ | $-CH_2CH=CH_2$ | Br | |
| 165 | $-(2\text{-F})C_6H_4$ | $-(4\text{-F})C_6H_4$ | $-CH_2C_6H_5$ | Br | 173 |

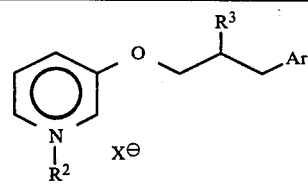

| No. | Ar | R$^2$ | R$^3$ | X | m.p. [°C.] |
|---|---|---|---|---|---|
| 166 | $-(4\text{-Cl})C_6H_4$ | $CH_3$ | $CH_3$ | Br | |
| 167 | $-(4\text{-Cl})C_6H_4$ | $CH_3$ | $CH_3$ | I | |
| 168 | $-(4\text{-Cl})C_6H_4$ | $-CH_2-CH=CH_2$ | $CH_3$ | Br | |
| 169 | $-(4\text{-Cl})C_6H_4$ | $-CH_2C_6H_5$ | $CH_3$ | Br | |
| 170 | $-(4\text{-C(CH}_3)_3)C_6H_4$ | $CH_3$ | $CH_3$ | Br | |
| 171 | $-(4\text{-C(CH}_3)_3)C_6H_4$ | $CH_3$ | $CH_3$ | I | |
| 172 | $-(4\text{-C(CH}_3)_3)C_6H_4$ | $-CH_2CH=CH_2$ | $CH_3$ | Br | |
| 173 | $-(4\text{-C(CH}_3)_3)C_6H_4$ | $-CH_2C_6H_5$ | $CH_3$ | Br | |

| | Characteristic $^1$H-NMR data | |
|---|---|---|
| Compound no. | Solvent | Chemical shift in ppm |
| 96 | d$_6$-DMSO | s 5.9 [2H], broadened dd 8.15 [1H]; broadened d 8.30 [1H], d 8.90 [1H]; s 9.25 [1H] |
| 119 | d$_6$-DMSO | s 5.92 [2H], dd 8.10 [1H]; broadened d 8.28 [1H], d 8.92 [1H]; s 9.28 [1H] |
| 137 | d$_6$-DMSO | s 4.35 [3H], dd 8.05 [1H]; broadened d 8.20 [1H], d 8.62 [1H]; s 8.92 [1H] |
| 149 | CDCl$_3$ | s 6.15 [2H], broadened dd 7.79 [1H]; broadened d 7.98 [1H], d 9.09 [1H]; s 9.52 [1H] |
| 157 | d$_6$-DMSO | s 5.85 [2H], dd 8.10 [1H]; broadened d 8.35 [1H], d 8.90 [1H]; s 9.40 [1H] |

The active ingredients are for the prevention and cure of plant diseases caused by phytopathogenic fungi, particularly those from the Asomycetes and Phycomycetes classes. Some of them have a systemic action and can be used as foliar and soil fungicides.

The fungicidal compounds are of particular interest for controlling a large number of fungi in various crops or their seeds, in particular wheat, rye, barley, oats, rice, corn, cotton, soybean, coffee, sugar cane, fruit and ornamentals in horticulture, in viticulture, and for vegetables, such as cucumbers, beans and Cucurbitaceae.

The novel compounds are particularly useful for controlling the following plant diseases:

Erysiphe graminis in cereals,
Erysiphe cichoracearum and Sphaerotheca fuliginea in Cucurbitaceae,
Podosphaera leucotricha in apples,
Uncinula necator in vines,
Puccinia species in cereals,
Rhizoctonia solani in cotton and lawns,
Ustilago species in cereals and sugar cane,
Venturia inaequalis (scab) in apples,
Septoria nodorum in wheat,
Botrytis cinerea (gray mold) in strawberries and vines,
Cercospora arachidicola in groundnuts,
Pseudocercosporella herpotrichoides in wheat and barley,
Pyrenophora teres in barley,
Pyricularia oryzae in rice,
Hemileia vastatrix in coffee,
Phytophthora infestans and Alternaria solani in potatoes and tomatoes,
Plasmopara viticola in grapes, and
Fusarium and Verticillium species in various plants.

The compounds are applied by spraying or dusting plants with the active ingredients, or treating the seeds of the plants with the active ingredients. They are applied before or after infection of the plants or seeds by the fungi.

The novel substances can be converted to the conventional formulations, such as solutions, emulsions, suspensions, dusts, powders, pastes and granules. The forms for use depend entirely on the purposes for which they are intended; they should at all events ensure a fine and uniform distribution of the active substance. The formulations are produced in a known manner, for example by extending the active ingredients with solvents and/or carriers, with or without the use of emulsifiers and dispersants; if water is used as a diluent, it is also possible to employ other, organic solvents as auxiliary solvents. Suitable assistants for this purpose are essentially solvents, such as aromatics (eg. xylene or benzene), chlorinated aromatics (eg. chlorobenzenes), paraffins (eg. oil fractions), alcohols (eg. methanol or butanol), amines (eg. ethanolamine or dimethylformamide) and water; carriers, such as ground natural minerals (kaolins, aluminas, talc or chalk) and ground synthetic minerals (eg. highly disperse silica or silicates), emulsifiers, such as nonionic and anionic emulsifiers (eg. polyoxyethylene fatty alcohol ethers, alkylsulfonates and arylsulfonates) and dispersants, such as lignin, sulfite waste liquors and methylcellulose.

The fungicides generally contain from 0.1 to 95, preferably from 0.5 to 90, % by weight of active ingredient.

The application rates are from 0.1 to 3 kg or more of active ingredient per hectare, depending on the type of effect desired. The agents and the ready-to-use formulations prepared from them, such as solutions, emulsions, suspensions, powders, dusts, pastes or granules, are applied in a conventional manner, for example by spraying, atomizing, dusting, scattering, dressing or watering.

Examples of such formulations are:

I. 90 parts by weight of compound no. 11 is mixed with 10 parts by weight of N-methyl-alpha-pyrollidone. A mixture is obtained which is suitable for application in the form of very fine drops.

II. 20 parts by weight of compound no. 12 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 13 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 14 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 23 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 25 is intimately mixed with 97 parts by weight of particulate kaolin. A dust is obtained containing 3% by weight of the active ingredient.

VII. 30 parts by weight of compound no. 28 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 29 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts of compound no. 30 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

In these application forms, the agents according to the invention may also be present together with other active ingredients, for example herbicides, insecticides, growth regulators and fungicides, or may furthermore be mixed with fertilizers and applied together with these. Mixing with fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:
sulfur
dithiocarbamates and derivatives thereof, such as
  ferric dimethyldithiocarbamate
  zinc dimethyldithiocarbamate
  zinc ethylenebisthiocarbamate
  manganese ethylenebisdithiocarbamate
  manganese zinc ethylenediaminebisdithiocarbamate
  tetramethylthiuram disulfides
  ammonia complex of zinc N,N'-ethylenebisdithiocarbamate
  ammonia complex of zinc N,N-propylenebisdithiocarbamate
  zinc N,N'-propylenebisdithiocarbamate and
N,N-polypropylenebis(thiocarbamyl)disulfide
nitro derivatives, such as
  dinitro (1-methylheptyl)-phenyl crotonate
  2-sec-butyl-4,6-dinitrophenyl-3,3-dimethylacrylate
  2-sec-butyl-4,6-dinitrophenyl isopropylcarbonate and
  diisopropyl 5-nitroisophthalate
heterocyclic substances, such as
  2-heptadecylimidazol-2-yl acetate
  2,4-dichloro-6-(o-chloroanilino)-s-triazine
  O,O-diethyl phthalimidophosphonothionate
  5-amino-1-[bis-(dimethylamino)-phosphinyl]-3-phenyl-1,2,4-triazole
  2,3-dicyano-1,4-dithiaanthraquinone
  2-thio-1,3-dithio-[4,5-b]-quinoxaline
  methyl 1-(butylcarbamoyl)-2-benzimidazole carbamate
  2-methoxycarbonylaminobenzimidazole
  2-[furyl-(2)]-benzimidazole
  2-[thiazolyl-(4)]-benzimidazole
  N-(1,1,2,2-tetrachloroethylthio)-tetrahydrophthalimide
  N-trichloromethylthiotetrahydrophthalimide
  N-trichloromethylthiophthalimide
  N-dichlorofluoromethylthio-N',N'-dimethyl-N-phenyl-sulfuric acid diamide
  5-ethoxy-3-trichloromethyl-1,2,3-thiadiazole
  2-thiocyanomethylthiobenzthiazole
  1,4-dichloro-2,5-dimethoxybenzole
  4-(2-chlorophenylhydrazono)-3-methyl-5-isoxazolone
  2-thiopyridine 1-oxide
  8-hydroxyquinoline and its copper salt
  2,3-dihydro-5-carboxanilido-6-methyl-1,4-oxathiin
  2,3-dihydro-5-carboxanilido-6-methyl-1,4-oxathiin 4,4-dioxide
  2-methyl-5,6-dihydro-4-H-pyran-3-carboxanilide
  2-methylfuran-3-carboxanilide
  2,5-dimethylfuran-3-carboxanilide
  2,4,5-trimethylfuran-3-carboxanilide
  2,5-dimethyl-N-cyclohexylfuran-3-carboxamide
  N-cyclohexyl-N-methoxy-2,5-dimethyl-furan-3-carboxamide
  2-methylbenzanilide
  2-iodobenzanilide
  N-formyl-N-morpholine-2,2,2-trichloroethylacetal
  piperazine-1,4-diylbis-(1-(2,2,2-trichloroethyl)-formamide
  1-(3,4-dichloroanilino)-1-formylamino-2,2,2-trichloroethane
  2,6-dimethyl-N-tridecyl-morpholine and its salts
  2,6-dimethyl-N-cyclododecyl-morpholine and its salts
  N-[3-(p-tert.-butylphenyl)-2-methylpropyl]-cis-2,6-dimethylmorpholine
  N-[3-(p-tert.-butylphenyl)-2-methylpropyl]-piperidine
  1-[2-(2,4-dichlorophenyl)-4-ethyl-1,3-dioxolan-2-yl-ethyl]-1-H-1,2,4-triazole
  1-[2-(2,4-dichlorophenyl)-4-n-propyl-1,3-dioxolan-2-yl-ethyl]-1-H-1,2,4-triazole
  N-(n-propyl)-N-(2,4,6-trichlorophenoxyethyl)-N+-imidazolylurea
  1-(4-chlorophenoxy)-3,3-dimethyl-1-(1H-1,2,4-triazol-1-yl)-butan-2-one
  1-(4-chlorophenoxy)-3,3-dimethyl-1-(1H-1,2,4-triazol-1-yl)butan-2-ol
  1-(4-phenylphenoxy-3,3-dimethyl-1-(1H-1,2,4-triazol-1-yl)-2-butanol
  alpha-(2-chlorophenyl)-alpha-(4-chlorophenyl)-5-pyrimidinemethanol
  5-butyl-2-dimethylamino-4-hydroxy-6-methylpyrimidine
  bis-(p-chlorophenyl)-3-pyridinemethanol
  1,2-bis-(3-ethoxycarbonyl-2-thioureido)-benzene
  1,2-bis-(3-methoxycarbonyl-2-thioureido)-benzene
and various fungicides, such as
  dodecylguanidine acetate
  3-[2-(3,5-dimethyl-2-oxycyclohexyl)-2-hydroxyethyl]-glutaramide
  hexachlorobenzene
  DL-methyl-N-(2,6-dimethylphenyl)-N-fur-2-yl alanate
  methyl DL-N-(2,6-dimethylphenyl)-N-(2'-methoxyacetyl)-alanate
  N-(2,6-dimethylphenyl)-N-chloroacetyl-DL-2-aminobutyrolactone
  methyl DL-N-(2,6-dimethylphenyl)-N-(phenylacetyl)-alanate
  5-methyl-5-vinyl-3-(3,5-dichlorophenyl)-2,4-dioxo-1,3-oxazolidine
  3-(3,5-dichlorophenyl)-5-methyl-5-methoxymethyl-1,3-oxazolidine-2,4-dione
  3-(3,5-dichlorophenyl)-1-isopropylcarbamoylhydantoin
  N-(3,5-dichlorophenyl)-1,2-dimethyl-cyclopropane-1,2-dicarboximide 2-cyano-[N-(ethylaminocarbonyl)-2-methoximino]-acetamide
1-[2-(2,4-dichlorophenyl)-pentyl]-1H-1,2,4-triazole
2,4-dilfuoro-alpha-(1H-1,2,4-triazol-1-ylmethyl)-benzhydryl alcohol and
N-(n-propyl)-N-(2,4,6-trichlorophenoxyethyl)-N'-imidazolylurea.

For the following experiments, the prior art compound N-trichloromethylthiotetrahydrophthalimide (A) was used for comparison process.

USE EXAMPLE 1

Action on *Botrytis cinerea* in pimientos

Pimiento seedlings of the "Neusielder Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus *Botrytis cinerea*, and placed at 22° to 24° C. in a chamber of high humidity. After 5 days, the disease had spread to such a great extent on the untreated plants that the necroses covered the major portion of the leaves.

The results of this experiment show that cmpounds 11, 12, 13, 14, 23, 25, 27, 28, 29, 30, 40 and 41, applied as 0.05 wt% spray liquors, have a better fungicidal action (e.g., 97%) than comparative compound A (70%).

USE EXAMPLE 2

Action on *Phytophthora infestans* in tomatoes

Leaves of potted tomatoes of the "Große Fleischtomate" variety were sprayed with aqueous liquors containing (dry basis) 80% of active ingredient and 20% of emulsifier. After the sprayed-on layer had dried, the leaves were infected with a zoospore suspension of *Phytophthora infestans*. The plants were then placed for 5 days in a water vapor-saturated chamber kept at 16° to 18° C. After this period, the disease had spread on the untreated control plants to such an extent that the fungicidal action of the compounds was able to be assessed.

The results of this experiment show that compounds 6, 9, 11, 12, 13, 14, 22, 23, 25, 27, 30, 32, 40, 41, 60 and 61, applied as 0.025% spry liquors, have a better fungicidal action (90%) than compound A (60%).

USE EXAMPLE 3

Action on *Pyricularia oryzae* (protective)

Leaves of pot-grown rice seedlings of the "Bahia" variety were sprayed to runoff with aqueous emulsions consisting (dry basis) of 80% of active ingredient and 20% of emulsifier, and inoculated 24 hours later with an aqueous spore suspension of *Pyricularia oryzae*. The plants were then set up in climatic cabinets at 22° to 24° C. and a relative humidity of 95 to 99%. The extent of fungus spread was determined after 6 days.

The results of this experiment show that compounds 5, 7, 23 and 40, applied as 0.05% spray liquors, had a good fungicidal action (e.g. 97%).

USE EXAMPLE 4

Action on *Septoria nodorum*

Leaves of pot-grown wheat seedlings of the "Jubilar" variety were sprayed to runoff with aqueous spray liquors consisting (dry basis) of 80% of active ingredient and 20% of emulsifier. On the following day, the plants (with the dried-on layer) were infected with an aqueous spore suspension of *Septoria nodorum*, and then cultivated for a further 10 days at 17° to 19° C. and a relative humidity of 95%. The extent of fungus attack was then assessed visually.

The results of this experiment show that compounds 5, 7, 23, 40, 60, 61, 146, 149, 157, 159, 161 and 163 have a good fungicidal action (e.g., 97%).

We claim:

1. An O-substituted 3-oxypyridinium salt of the formula

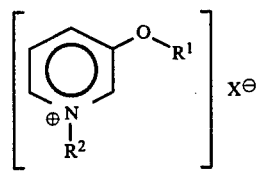

where $R^1$ is an alkyl, alkenyl or alkynyl radical which contains a total of 8 to 20 carbon atoms and is unsubstituted or substituted by halogen, or is $-C_2-C_{10}$-alkyl—O—$C_5$—$C_{18}$-alkyl which contains a total of 10 to 20 carbon atoms and may contain 1 or 2 double bonds or one triple bond which are or is separated from O by one or more $CH_2$ groups, or $R^1$ is

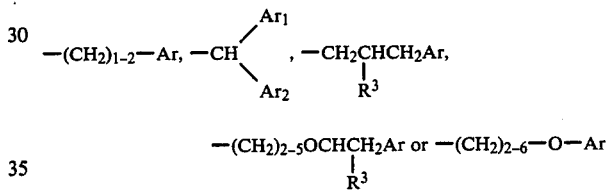

where Ar, $Ar_1$ are each 1- or 2-naphthyl, biphenyl or phenyl, and the phenyl radical may be substituted by F, Cl, Br, $NO_2$, $CF_3$, CN, $C_1$-$C_{13}$—alkyl, $C_2$-$C_4$—alkenyl or $C_1$— or $C_2$—alkoxy and $R^3$ is H, $C_1$— or $C_2$—alkyl, $C_3$-$C_5$—alkenyl or $C_1$-$C_5$—alkoxy, $R^2$ is an alkyl, alkenyl or alkynyl radical of 1 to 2 or 3 to 8 carbon atoms which is unsubstituted or substituted by $C_1$-$C_4$—alkoxy or halogen, or $R^2$ is

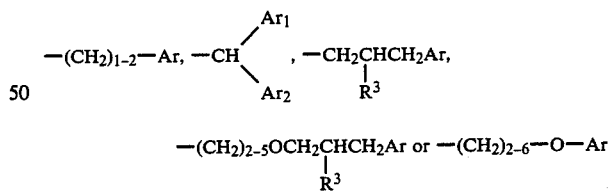

where Ar, $Ar_1$ are each 1- or 2-naphthyl, biphenyl or phenyl, and the phenyl radical may be substituted by F, Cl, Br, $NO_2$, $CF_3$, CN, $C_1$-$C_3$—alkyl, $C_2$-$C_4$—alkenyl or $C_1$— or $C_2$—alkoxy, and $X^-$ is $F^-$, $Cl^-$, $Br^-$ or $I^-$ or one equivalent of an anion of a non-phytotoxic acid.

2. An O-substituted 3-oxypyridinium salt of the formula I as set forth in claim 1, where $R^1$ is straight-chain or branched decyl, undecyl, tridecyl, tetradecyl, pentadecyl, hexadecyl, heptadecyl or octadecyl, which is unsubstituted or substituted by 2–5 Cl or F atoms, or is $-C_2-C_{10}$—alkyl—O—$C_5$-$C_{18}$—alkyl which contains a total of 10 to 20 carbon atoms and may contain 1 or 2 double bonds or one triple bond, or a radical

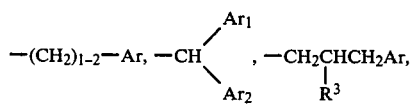, 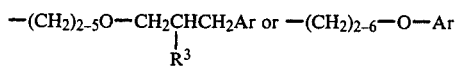

where Ar, Ar$_1$ and Ar$_2$ are each 1- or 2-naphthyl, biphenyl, phenyl, monosubstituted, disubstituted or trisubstituted phenyl, 4-fluorophenyl, 3- or 4-chlorophenyl, 4-bromophenyl, 3,4-dichlorophenyl, 2,4-dichlorophenyl, 2,6-dichlorophenyl, 2,4,6-trichlorophenyl, 2-methyl-4-chlorophenyl, 4-methoxyphenyl, 4-ethoxyphenyl, 4-methylphenyl, 4-nitrophenyl, 4-tert.-butylphenyl, 4-dodecylphenyl, 4-trifluoromethylphenyl, 2-trifluoromethyl-4-chlorophenyl, 2,4-dimethylphenyl, 2,4,6-trimethylphenyl or 4-cyanophenyl, $R^3$ is hydrogen, methyl or ethyl, $R^2$ is methyl, ethyl, propyl, isopropyl, n-butyl, isobutyl, n-pentyl, isopentyl, n-hexyl, allyl, 2-chloropropenyl, 2-bromophenyl, 3-chloropropenyl, but-2-en-1-yl, 3-methylbut-2-en-1-yl, 2-methylpropenyl, 3-chlorobut-2-en-1-yl, propargyl or a radical

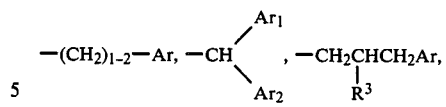, 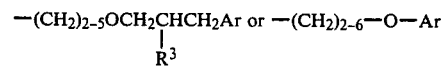

where Ar, Ar$_1$ and Ar$_2$ are each 1- or 2-naphthyl, biphenyl phenyl, monosubstituted, disubstituted or trisubstituted phenyl, 4-fluorophenyl, 3- or 4-chlorophenyl, 4-bromophenyl, 3,4-dichlorophenyl, 2,4-dichlorophenyl, 2,6-dichlorophenyl, 2,4,6-trichlorophenyl, 2-methyl-4-chlorophenyl, 4-methoxyphenyl, 4-ethoxyphenyl, 4-methylphenyl, 4-nitrophenyl, 4-tert.-butylphenyl, 4-dodecylphenyl, 4-trifluoromethylphenyl, 2-trifluoromethyl-4-chlorophenyl, 2,4-dimethylphenyl, 2,4,6-trimethylphenyl or 4-cyanophenyl, and $X^\ominus$ is $Cl^\ominus$, $Br^\ominus$, $I^\ominus$ or one equivalent of an anion of a non-phytotoxic acid.

3. A fungicidal composition for crop protection, containing a solid or liquid carrier and a fungicidally effective amount of an o-substituted 3-oxypyridinium salt as set forth in claim 1.

4. A process for combatting phytopathogenic fungi which comprises administering a fungicidally effective amount of an o-substituted 3-oxypyridinium salts as set forth in claim 1 to plants or seed to kill phytopathogenic fungus or to protect said plants or seed from said fungus attack.

* * * * *